US008360981B2

(12) United States Patent
Miyachi

(10) Patent No.: US 8,360,981 B2
(45) Date of Patent: Jan. 29, 2013

(54) ULTRASONIC DIAGNOSTIC APPARATUS

(75) Inventor: Yukiya Miyachi, Kaisei-machi (JP)

(73) Assignee: Fujifilm Corporation (JP)

( * ) Notice: Subject to any disclaimer, the term of this patent is extended or adjusted under 35 U.S.C. 154(b) by 572 days.

(21) Appl. No.: 12/541,822

(22) Filed: Aug. 14, 2009

(65) Prior Publication Data

US 2010/0049048 A1    Feb. 25, 2010

(30) Foreign Application Priority Data

Aug. 22, 2008  (JP) ................. 2008-214137

(51) Int. Cl.
A61B 8/14  (2006.01)

(52) U.S. Cl. .............. 600/459; 600/443; 382/128

(58) Field of Classification Search .......... 600/443, 600/459; 382/128; 348/333.13, 440.1, 476–477, 348/634, 800; 396/301–304
See application file for complete search history.

(56) References Cited

U.S. PATENT DOCUMENTS 7,173,599 B2* 2/2007 Nishimura ............. 345/102
2007/0040954 A1* 2/2007 Lee et al. ............... 349/43

FOREIGN PATENT DOCUMENTS

JP 2003-066918 A 3/2003
JP 2005-512649 A 5/2005
WO 03/052452 A1 6/2003

* cited by examiner

Primary Examiner — Brian Casler
Assistant Examiner — Daniel Huntley
(74) Attorney, Agent, or Firm — Studebaker & Brackett PC; Donald R. Studebacker

(57) ABSTRACT

An ultrasonic diagnostic apparatus in which moving images of rapidly moving tissues and organs can be preferably displayed in real time and the lower power consumption can be achieved. The apparatus includes an ultrasonic probe including plural ultrasonic transducers for transmitting ultrasonic waves toward an object to be inspected according to drive signals and receiving ultrasonic echoes propagating from the object to output reception signals, an image generating unit for supplying the drive signals to the ultrasonic probe and processing the reception signals outputted from the ultrasonic probe to generate image signals representing ultrasonic images, and a display unit including a display of an impulse drive type for displaying the ultrasonic images based on the image signals generated by the image generating unit.

11 Claims, 10 Drawing Sheets

HOLD TYPE	IMPULSE DRIVE TYPE

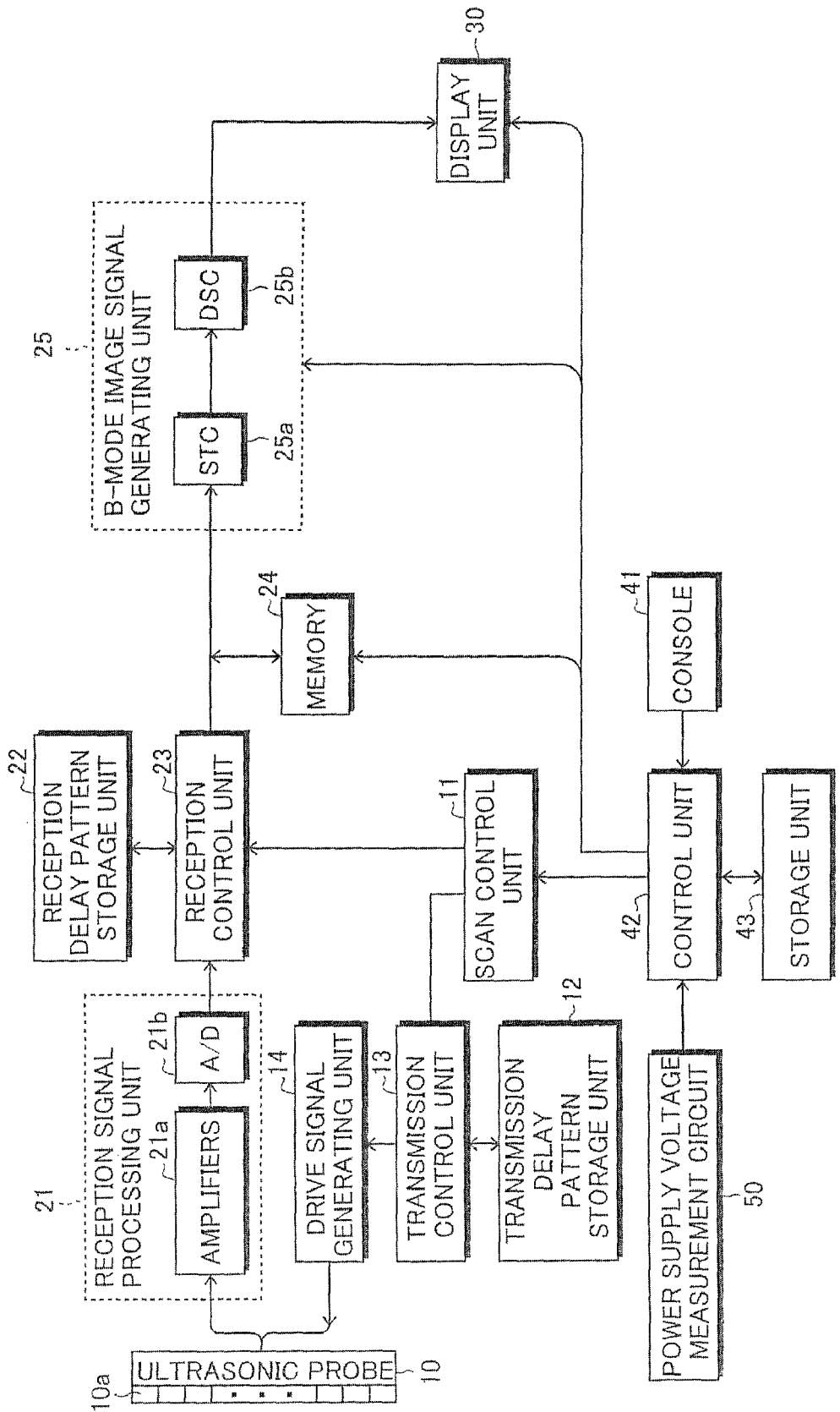

ULTRASONIC DIAGNOSTIC APPARATUS

CROSS-REFERENCE TO RELATED APPLICATION

The present application claims priority from Japanese Patent Application No. 2008-214137 filed on Aug. 22, 2008, the contents of which are incorporated herein by reference in their entirety.

BACKGROUND OF THE INVENTION

1. Field of the Invention

The present invention relates to an ultrasonic diagnostic apparatus for imaging organs within a living body and so on by transmitting and receiving ultrasonic waves to generate ultrasonic images to be used for diagnoses.

2. Description of a Related Art

In medical fields, various imaging technologies have been developed for observation and diagnoses within an object to be inspected. Especially, ultrasonic imaging for acquiring interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in obstetrics but also gynecology, circulatory system, digestive system, and so on.

Generally, in an ultrasonic diagnostic apparatus, an ultrasonic probe including plural ultrasonic transducers having transmission and reception functions of ultrasonic waves is used. By using such an ultrasonic probe, an object to be inspected is scanned with an ultrasonic beam formed by synthesizing plural ultrasonic waves, ultrasonic echoes reflected within the object are received and reception focusing processing is performed, and thereby, image information on structures (e.g., internal organs, diseased tissues, and so on) existing within the object can be obtained based on intensity of the ultrasonic echoes and an ultrasonic image is displayed on a display unit.

Recently, in an ultrasonic diagnostic apparatus, the performance capable of preferably displaying moving images of rapidly moving tissues and organs in real time is required. Further, in a portable type ultrasonic diagnostic apparatus that can be battery-powered, lower power consumption is required.

As related technologies, Japanese Patent Application Publication JP-P2005-512649A (International Publication WO 03/052152 A1) discloses an ultrasonic imaging system having an image display that has a response time suitable for optimally displaying rapidly moving tissues and organs. The ultrasonic imaging system includes a system chassis, an ultrasonic scanhead coupled to the system chassis, and an organic light emitting device display coupled to the system chassis. The display includes a viewing screen on which an ultrasonic image can be displayed with superior response time, contrast ratios, and viewing angles.

Further, Japanese Patent Application Publication JP-P2003-66918A discloses a display device in which image deterioration due to moving image blurs or the like can be suppressed while upsizing and complication of the structure are suppressed. The display device includes a display element array in which drain wires and gate wires are formed in a matrix form, a drain driver for supplying a gradation voltage according to an image to the display elements, a gate driver for scanning lines of the display elements for supplying the gradation voltage, a data control circuit for inserting blanking data into image data for one frame period of the image, and a timing control circuit for generating clocks for scanning the lines of the display elements such that the image data and the blanking data are displayed within the one frame period on arbitrary display elements.

SUMMARY OF THE INVENTION

The present invention has been achieved in view of the above-mentioned points. A purpose of the present invention is to provide an ultrasonic diagnostic apparatus in which moving images of rapidly moving tissues and organs can be preferably displayed in real time and the lower power consumption can be achieved.

In order to accomplish the above-mentioned purposes, an ultrasonic diagnostic apparatus according to one aspect of the present invention includes: an ultrasonic probe including plural ultrasonic transducers for transmitting ultrasonic waves toward an object to be inspected according to drive signals and receiving ultrasonic echoes propagating from the object to output reception signals; image generating means for supplying the drive signals to the ultrasonic probe and processing the reception signals outputted from the ultrasonic probe to generate image signals representing ultrasonic images; and a display unit including a display of an impulse drive type for displaying the ultrasonic images based on the image signals generated by the image generating means.

According to the one aspect of the present invention, by using the display of the impulse drive type, moving images of rapidly moving tissues and organs can be preferably displayed in real time and the lower power consumption can be achieved.

BRIEF DESCRIPTION OF THE DRAWINGS

FIG. 6 is a block diagram showing a configuration of an ultrasonic diagnostic apparatus according to the second embodiment of the present invention;

DESCRIPTION OF THE PREFERRED EMBODIMENTS

Figure 1:
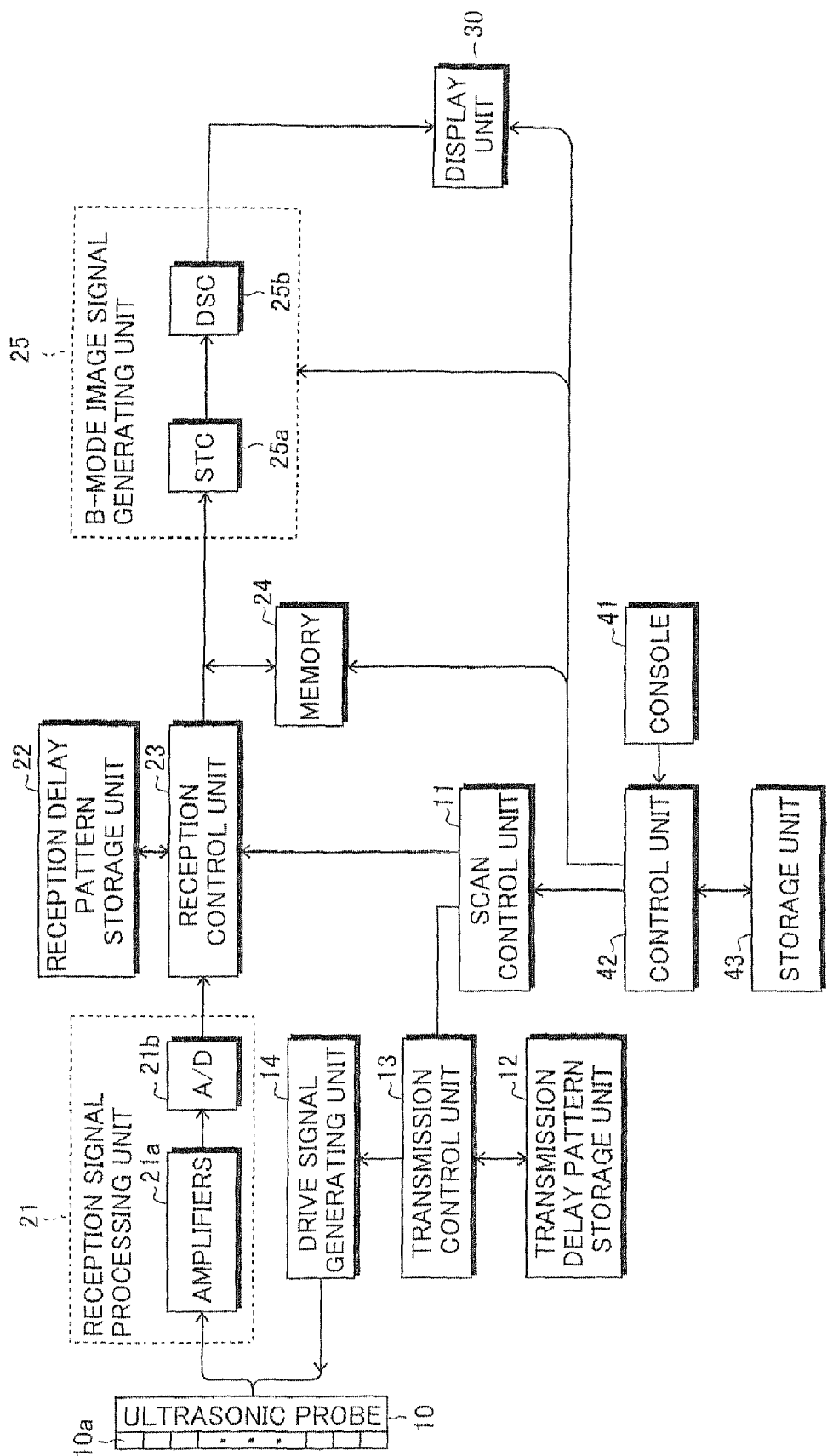
FIG. 1 is a block diagram showing a configuration of an ultrasonic diagnostic apparatus according to the first embodiment of the present invention.

Hereinafter, embodiments of the present invention will be described in detail with reference to the drawings. The same reference numerals will be assigned to the same component elements and the description thereof will be omitted.

FIG. 1 is a block diagram showing a configuration of an ultrasonic diagnostic apparatus according to the first embodiment of the present invention. The ultrasonic diagnostic apparatus includes an ultrasonic probe 10, a scan control unit 11, a transmission delay pattern storage unit 12, a transmission control unit 13, a drive signal generating unit 14, a reception signal processing unit 21, a reception delay pattern storage unit 22, a reception control unit 23, a memory 24, a B-mode image signal generating unit 25, a display unit 30, a console 41, a control unit 42, and a storage unit 43. Here, the scan control unit 11 to B-mode image signal generating unit 25 form image generating means.

The ultrasonic probe 10 may be an external probe of a linear scan type, convex scan type, sector scan type, or the like, or a probe for an ultrasonic endoscope, of an electronic radial scan type, mechanical radial scan type, or the like. The ultrasonic probe 10 includes plural ultrasonic transducers 10a forming a one-dimensional or two-dimensional transducer array. These ultrasonic transducers 10a transmit ultrasonic waves according to applied drive signals, and receive propagating ultrasonic echoes to output reception signals.

Each ultrasonic transducer includes a vibrator having electrodes formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like. When a pulsed or continuous wave voltage is applied to the electrodes of the vibrator, the piezoelectric material expands and contracts. By the expansion and contraction, pulse or continuous wave ultrasonic waves are generated from the respective vibrators, and an ultrasonic beam is formed by synthesizing these ultrasonic waves. Further, the respective vibrators expand and contract by receiving the propagating ultrasonic waves to generate electric signals. These electric signals are outputted as reception signals of ultrasonic waves.

The scan control unit 11 sequentially sets the transmission directions of ultrasonic beams and the reception directions of ultrasonic echoes. Scanning of an object to be inspected with the ultrasonic beams can be performed electrically or mechanically. The transmission delay pattern storage unit 12 has stored plural transmission delay patterns to be used when ultrasonic beams are formed. The transmission control unit 13 selects a transmission delay pattern from among the plural transmission delay patterns stored in the transmission delay pattern storage unit 12 according to the transmission direction set in the scan control unit 11, and sets delay times to be provided to drive signals of the plural ultrasonic transducers 10a based on the selected transmission delay pattern. Alternatively, the transmission control unit 13 may set delay times such that the ultrasonic waves transmitted at a time from the plural ultrasonic transducers 10a reach the entire imaging region of the object.

The drive signal generating unit 14 includes plural pulsers corresponding to the plural ultrasonic transducers 10a, for example. The drive signal generating unit 14 supply drive signals to the ultrasonic probe 10 such that the ultrasonic waves transmitted from the plural ultrasonic transducers 10a form an ultrasonic beam according to the delay times set by the transmission control unit 13, or supply drive signals such that the ultrasonic waves transmitted at a time from the plural ultrasonic transducers 10a reach the entire imaging region of the object.

The reception signal processing unit 21 includes plural preamplifiers 21a and plural A/D converters 21b corresponding to the plural ultrasonic transducers 10a. The reception signals outputted from the respective ultrasonic transducers 10a are amplified by the amplifiers 21a and the analog reception signals outputted from the amplifiers 21a are converted into digital reception signals by the A/D converters 21b. The A/D converters 21b output the digital reception signals to the reception control unit 23.

The reception delay pattern storage unit 22 has stored plural reception delay patterns to be used when focusing processing is performed on the reception signals outputted from the plural ultrasonic transducers 10a. The reception control unit 23 selects a reception delay pattern from among the plural reception delay patterns stored in the reception delay pattern storage unit 22 according to the reception direction set in the scan control unit 11, and performs reception focusing processing by providing delays to the reception signals based on the selected reception delay pattern, and adding the reception signals to one another. By the focusing processing, sound ray signals, in which the focus of the ultrasonic echoes is narrowed, are formed. Furthermore, the reception control unit 23 performs envelope detection processing on the formed sound ray signals.

The sound ray signals generated by the reception control unit 23 are supplied to the memory 24 and supplied to the B-mode image signal generating unit 25. The B-mode image signal generating unit 25 includes an STC (sensitivity time control) part 25a, and a DSC (digital scan converter) 25b, and B-mode image signals as tomographic image information on tissues within the object are generated based on the sound ray signals supplied from the reception control unit 23. Alternatively, in a freeze mode, B-mode image signals are generated based on the sound ray signals stored in the memory 24.

The STC part 25a performs attenuation correction by distance according to the depths of the reflection positions of ultrasonic waves on the sound ray signals supplied from the reception control unit 23 or memory 24. The DSC 25b converts (raster-converts) the sound ray signals corrected by the STC part 25a into image signals that follow the normal scan system of television signals and performs necessary image processing such as gradation processing to generate the B-mode image signals.

The display unit 30 includes an impulse drive type display, and displays ultrasonic images based on the B-mode image signals generated by the B-mode image signal generating unit 25. Further, in the display, it is desirable that the length of a blanking period in one field period is variable.

The control unit 42 controls the scan control unit 11, the memory 24, the B-mode image signal generating unit 25, the display unit 30, and so on according to an operation of an operator using the console 41. In the embodiment, the scan control unit 11, the transmission control unit 13, the reception control unit 23, the B-mode image signal generating unit 25, and the control unit 42 are formed of a CPU and software (program), however, they may be formed of digital circuits or analog circuits. The above-mentioned software (program) is stored in the storage unit 43. As a recording medium in the storage unit 43, not only a built-in hard disk but also a flexible disk, MO, MT, RAM, CD-ROM, DVD-ROM, or the like may be used.

Next, as an example of a display used in the display unit 30, an organic EL display of an active matrix type will be explained in detail with reference to FIGS. 2-5B.

Figure 2:
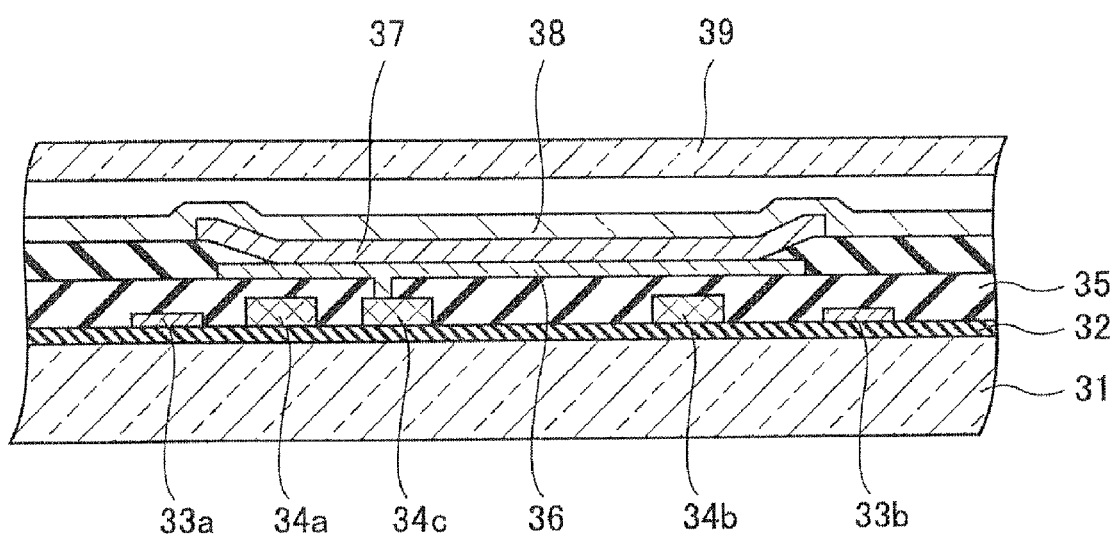
FIG. 2 is a sectional view schematically showing a structure of an organic EL display.

FIG. 2 is a sectional view schematically showing a structure of an organic EL display. On a transparent substrate 31 of glass or the like, plural wiring electrodes 33a and 33b, plural TFTs (thin-film transistors) 34a-34c, holding capacities, and so on are formed via an insulating film 32 for preventing entry of impurities. Further, an insulating film 35 including an interlayer insulating film and a planarizing film is formed to cover the wiring electrodes and so on, transparent electrodes 36 and organic EL (electro luminescence) elements 37 are formed thereon for respective pixels, and a common electrode 38 is formed further thereon. The organic EL element 37 includes a hole transport layer, a light emitting layer, and an electron transport layer. The transparent electrode 36 functions as an anode of the organic EL element 37, and the common electrode 38 functions as a cathode of the organic EL element 37. A sealing glass 39 is provided above the common electrode 38.

Figure 3:
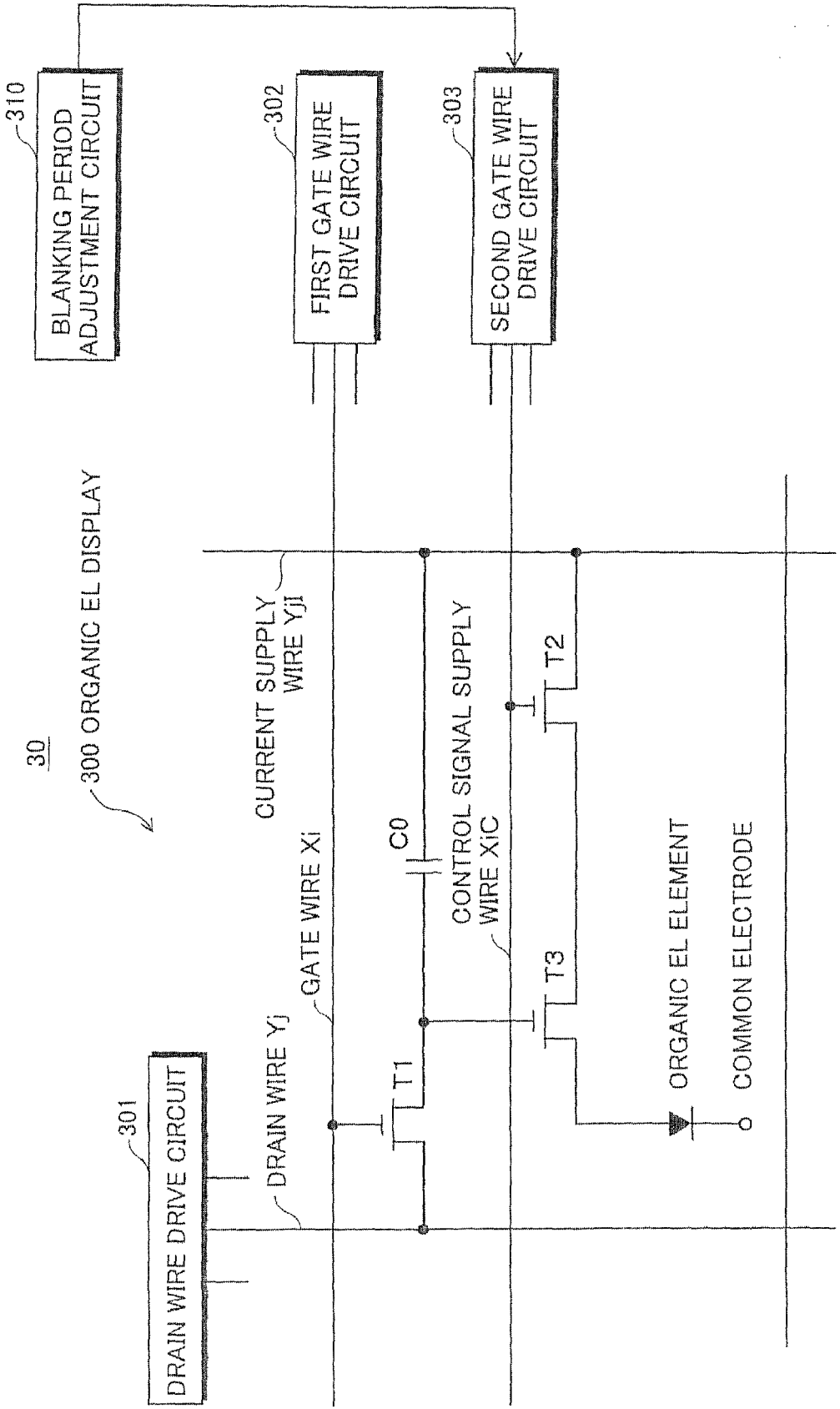
FIG. 3 shows a configuration example of a display unit used in the first embodiment of the present invention.

FIG. 3 shows a configuration example of a display unit used in the first embodiment of the present invention. The display unit includes an organic EL display 300, and a blanking period adjustment circuit 310 for adjusting a ratio of a blanking period to an image display period in one field period of the organic EL display 300.

The organic EL display 300 includes a drain wire drive circuit 301 for driving the drain wires Yj of the respective columns, a first gate wire drive circuit (gate wire drive circuit for scan line) 302 for driving the gate wires Xi of the respective rows (lines), a second gate wire drive circuit (gate wire drive circuit for controlling image display period) 303 for driving the control signal supply wires XiC of the respective rows, and the common electrode. A predetermined power supply voltage is applied to current supply wires YjI of the respective columns. Further, the organic EL display 300 includes, in each pixel, transistors (TFTs) T1-T3, a holding capacity C0, and an organic EL element equivalently represented by a diode.

The drain wire drive circuit 301 supplies image signals (analog voltages) of the respective columns to the drain wires Yj of the respective columns based on the B-mode image signals supplied by the B-mode image signal generating unit 25. The first gate wire drive circuit 302 activates gate voltages to be supplied to the gate wires Xi of the respective rows into the high level with predetermined timings. When the transistor T1 is turned on according to the gate voltage supplied via the gate wire Xi, the transistor T1 allows the holding capacity C0 to hold the image signal supplied via the drain wire Yj.

The blanking period adjustment circuit 310 outputs a signal, which specifies the ratio of the blanking period to the image display period, to the second gate wire drive circuit 303. The second gate wire drive circuit 303 generates control signals, which are activated into the high level in the image display periods of the respective rows and deactivated into the low level in the blanking periods, according to the signal output from the blanking period adjustment circuit 310, and supplies the control signals to the control signal supply wires XiC of the respective rows. The transistor T2 electrically connects the drain of the transistor T3 to the current supply wire YjI according to the control signal generated by the second gate wire drive circuit 303. The transistor T3 supplies a current from a source to the organic EL element according to the image signal held in the holding capacity C0 when the drain is electrically connected to the current supply wire YjI.

Figure 4:
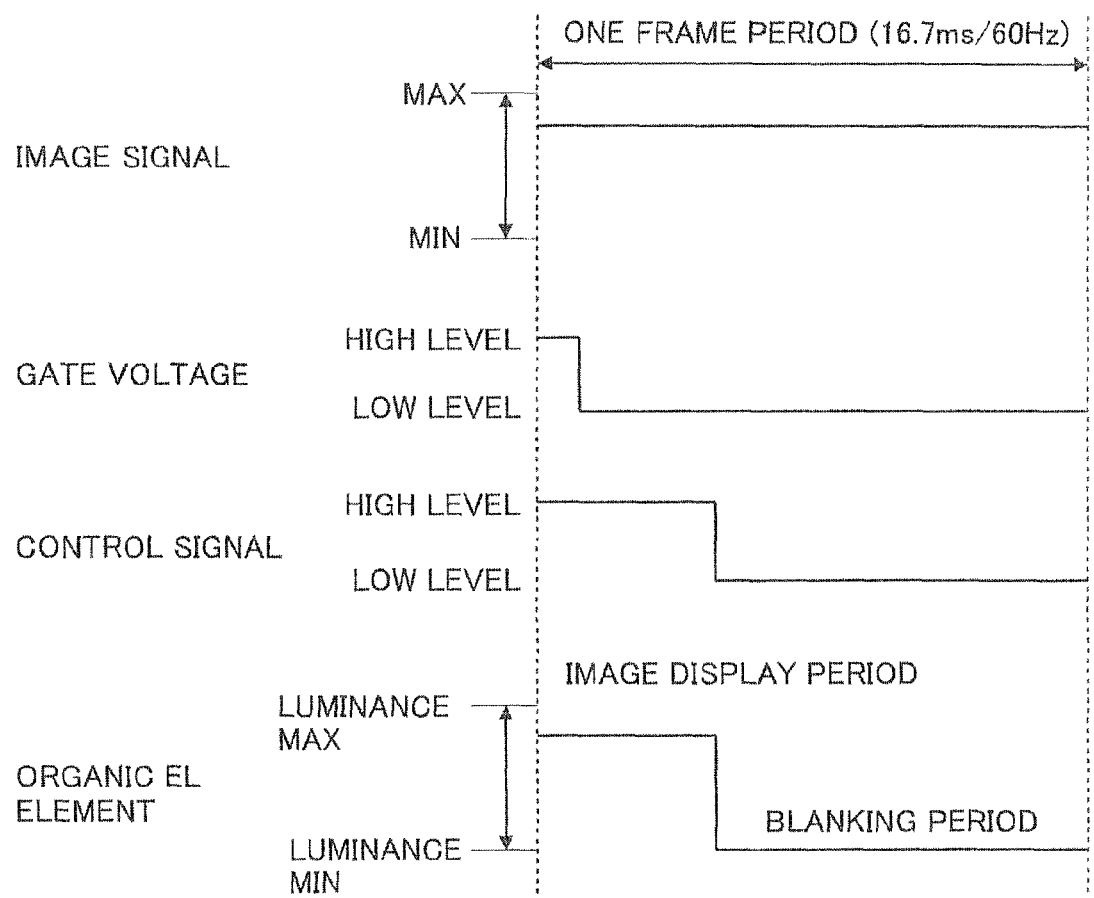
FIG. 4 is a timing chart for explanation of an operation of the display unit as shown in FIG. 3.

FIG. 4 is a timing chart for explanation of an operation of the display unit as shown in FIG. 3. FIG. 4 shows voltages of the respective parts and luminance of the organic EL element in one frame period of image display (about 16.7 ms when the frame rate is 60 Hz). In the interlace system, one frame includes plural fields, and the one frame period as shown in FIG. 4 is read as one field period. In the non-interlace system, one frame period is equivalent to one field period.

The voltage of the image signal supplied to the drain wire Yj takes a value between the maximum value (MAX) and the minimum value (MIN). When the gate voltage supplied via the gate wire Xi is activated into the high level at a certain time, the transistor T1 is turned on and the voltage of the image signal supplied via the drain wire Yj is held in the holding capacity C0.

In the period (image display period) in which the control signal is activated at the high level, the transistor T2 is turned on and the drain of the transistor T3 is electrically connected to the current supply wire YjI. Thereby, the transistor T3 flows a current in the organic EL element according to the voltage of the image signal held in the holding capacity C0, and the organic EL element emits light. The luminance of the organic EL element is proportional to the current flowing in the organic EL element, and takes a value between the luminance maximum value (MAX) and the luminance minimum value (MIN).

In the period (blanking period) in which the control signal is deactivated at the low level, the transistor T2 is turned off and the drain of the transistor T3 is electrically disconnected from the current supply wire YjI. Thereby, the transistor T3 flows no current in the organic EL element, and the organic EL element stops emitting light.

As described above, according to the embodiment, by turning on/off the transistor T2 according to the control signal generated by the second gate wire drive circuit 303, the period in which the organic EL element emits light can be adjusted.

Figure 5A:
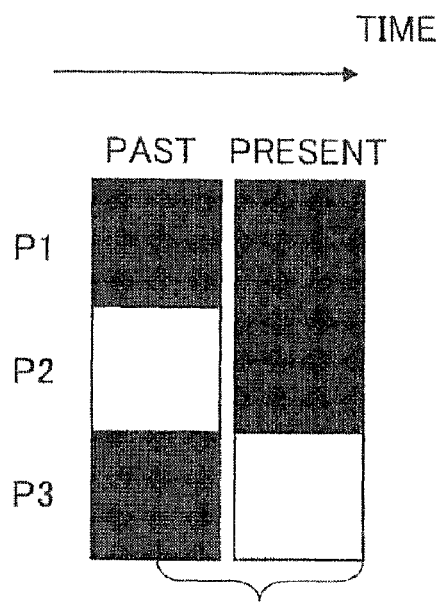
FIGS. 5A and 5B are diagrams in comparison of luminescent states between a hold type display and an impulse type drive display.
Figure 5B:
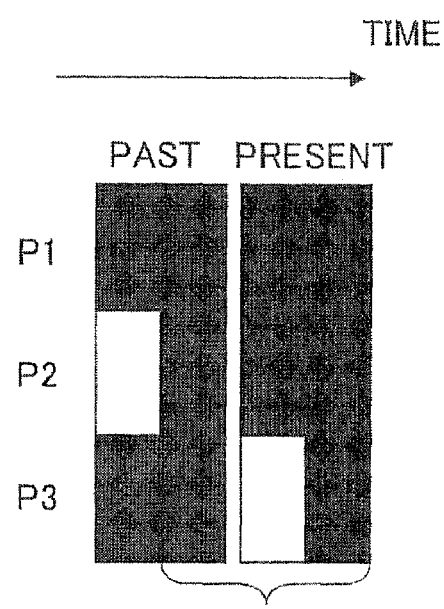

FIGS. 5A and 5B are diagrams in comparison of luminescent states between a hold type display and an impulse type drive display. FIGS. 5A and 5B show luminescent states in three pixels P1-P3 adjacent in the vertical direction. The upper part of FIG. 5A shows the luminescent state in the hold type display, and the luminescent states in the three pixels P1-P3 are fixed in one frame period. As a result, in the human eye, the luminescent state in a part of the past frame and the luminescent state in the current frame are integrated, and an afterimage occurs in the pixel P2 as shown in the lower part of FIG. 5A.

On the other hand, the upper part of FIG. 5B shows the luminescent state in the impulse drive type display, and the luminescent periods in the three pixels P1-P3 are limited in a predetermined period within one frame period. As a result, even when the luminescent state in a part of the past frame and the luminescent state in the current frame are integrated, an afterimage in the pixel P2 can be reduced as shown in the lower part of FIG. 5B. Therefore, moving images of rapidly moving tissues and organs can be preferably displayed in real time.

Further, the power consumption in each pixel is determined by a product of the current flowing in the organic EL element and the power supply voltage, and thus, the lower power consumption can be achieved by extending the blanking period. In this case, although luminance of the display becomes lower, the display of the ultrasonic diagnostic apparatus is often used within a dark room compared to a display for general use and the luminance of the display of the ultrasonic diagnostic apparatus is not so much required.

In the above configuration, if the blanking period is too short, moving image performance is not improved. However, extension of the blanking period has an upper limit. It is conceivable that desired luminance is obtained by increasing the current density in the organic EL element while extending the blanking period, however, if the current density in the organic EL element is increased too much, its life becomes shorter. Therefore, the ratio of the blanking period in one frame period (or one field period) is suitably 10% to 70%, more preferably 50% to 70%.

In the embodiment, the operator operates a button (icon) displayed on the screen of the display or operates a lever or dial provided on the console 41 shown in FIG. 1, and thereby, the blanking period adjustment circuit 310 as shown in FIG. 3 adjusts the ratio of the blanking period to the image display period in one field period of the display.

Alternatively, the control unit 42 as shown in FIG. 1 may control the blanking period adjustment circuit 310 to automatically adjust the ratio of the blanking period to the image display period in one field period of the display. For example, the control unit 42 adjusts the ratio of the blanking period to the image display period according to a part to be examined selected in presetting.

In an examination using an ultrasonic diagnostic apparatus, there are the case of observing a part moving at a high speed such as the heart of a fetus, especially, and the case of observing a part relatively stationary such as liver. In impulse drive, if the blanking period is set too long, the display performance of high-speed moving images is improved but there is a disadvantage that flicker of the screen is highly visible. Accordingly, the control unit 42 controls the blanking period adjustment circuit 310 to make the blanking period longer when the part moving at a high speed is observed, and make the blanking period shorter when the part relatively stationary is observed.

As described above, in the case where the ultrasonic diagnostic apparatus has a function of automatically adjusting the blanking period according to the part to be examined selected in the presetting, moving images preferable for the respective parts to be examined can be provided. When a still image is observed in the freeze mode, the control unit 42 controls the blanking period adjustment circuit 310 to make the blanking period shorter.

Further, in the examination using the ultrasonic diagnostic apparatus, in the case where the part moving at a high speed is observed, the frame rate of the image signals generated by the image generating means is generally set higher. Accordingly, the control unit 42 may control the blanking period adjustment circuit 310 to adjust the ratio of the blanking period to the image display period in one field period of the display according to the frame rate of the image signal generated by the image generating means.

Furthermore, in the case where the ultrasonic diagnostic apparatus can be set into an energy saving mode, the control unit 42 may determine whether or not the ultrasonic diagnostic apparatus has been set into the energy saving mode, and control the blanking period adjustment circuit 310 to adjust the ratio of the blanking period to the image display period in one field period of the display according to the determination result. Specifically, the control unit 42 controls the blanking period adjustment circuit 310 to set the blanking period longer when the ultrasonic diagnostic apparatus is set into the energy saving mode, and set the blanking period shorter when the ultrasonic diagnostic apparatus is not set into the energy saving mode.

Next, the second embodiment of the present invention will be explained.

FIG. 6 is a block diagram showing a configuration of an ultrasonic diagnostic apparatus according to the second embodiment of the present invention. In the second embodiment, a power supply voltage measurement circuit 50 is added to the ultrasonic diagnostic apparatus according to the first embodiment as shown in FIG. 1. The rest of the configuration is the same as that of the first embodiment.

In a portable type ultrasonic diagnostic apparatus, two driving methods of battery drive using an internal battery and external power supply drive using an outlet can be supported. In the case of external power supply drive, an external power supply is connected to an external power supply input terminal of a power supply circuit. Accordingly, the power supply voltage measurement circuit 50 measures a power supply voltage at the external power supply input terminal. Further, the control unit 42 determines whether battery drive or external power supply drive based on the power supply voltage measured by the power supply voltage measurement circuit 50, and controls the blanking period adjustment circuit 310 to adjust the ratio of the blanking period to the image display period in one field period of the display according to the determination result. Specifically, the control unit 42 controls the blanking period adjustment circuit 310 to make the blanking period longer in the case of battery drive and make the blanking period shorter in the case of external power supply drive.

Furthermore, the control unit 42 may change brightness of the display screen according to the determination result. Specifically, the control unit 42 controls the display unit 30 to reduce the brightness of the display screen in the case of battery drive and increase the brightness of the display screen in the case of external power supply drive.

Next, the third embodiment of the present invention will be explained.

Figure 7:
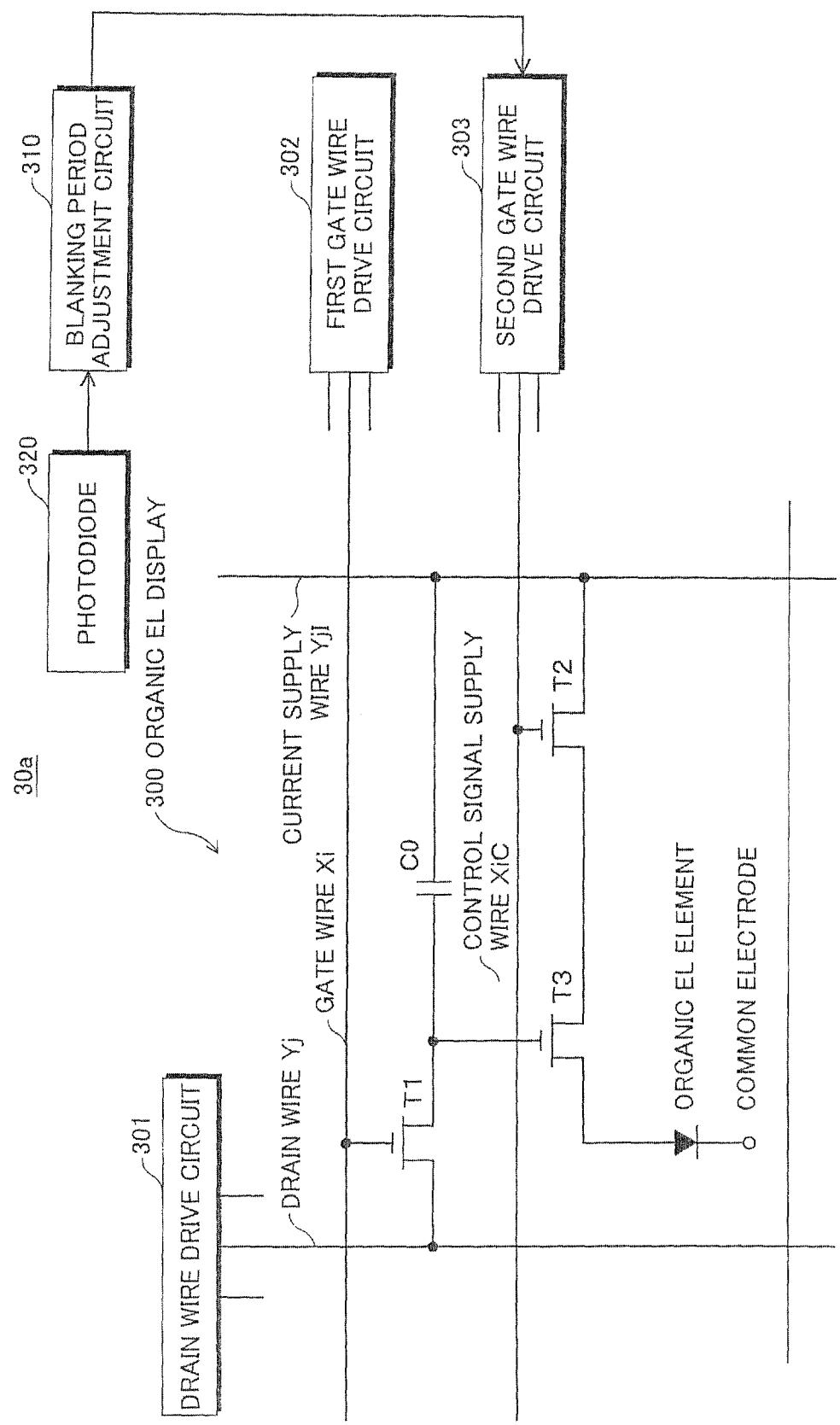
FIG. 7 shows a configuration example of a display unit used in the third embodiment of the present invention.

FIG. 7 shows a configuration example of a display unit used in the third embodiment of the present invention. In a display unit 30a, a photodiode 320 is added to the display unit 30 as shown in FIG. 1. The rest of the configuration is the same as that of the first embodiment.

The ultrasonic diagnostic apparatus is medical equipment to be used in a wide range of environments from inside a dark room to outside in bright light (emergency). Accordingly, the photodiode 320 is provided as brightness sensing means for sensing brightness around the display, and the blanking period adjustment circuit 310 adjusts the ratio of the blanking period to the image display period in one field period of the display according to a sensing result of the photodiode 320. Specifically, the blanking period adjustment circuit 310 increases the brightness by making the blanking period shorter when the brightness around the display is light, and reduces the brightness by making the blanking period longer when the brightness around the display is dark.

The photodiode 320 may be attached to a housing of the display 30 or the like of the ultrasonic diagnostic apparatus. Alternatively, the photodiode 320 may be formed via the insulating film 35 on the transparent substrate 31 of the organic EL display as shown in FIG. 2, and sense the brightness around the organic EL display when the power is on and the organic EL display still emits no light. Since the TFT is formed by using polysilicon or the like, the photodiode 320 for sensing visible light can be formed in the same process.

Next, the fourth embodiment of the present invention will be explained.

Figure 8:
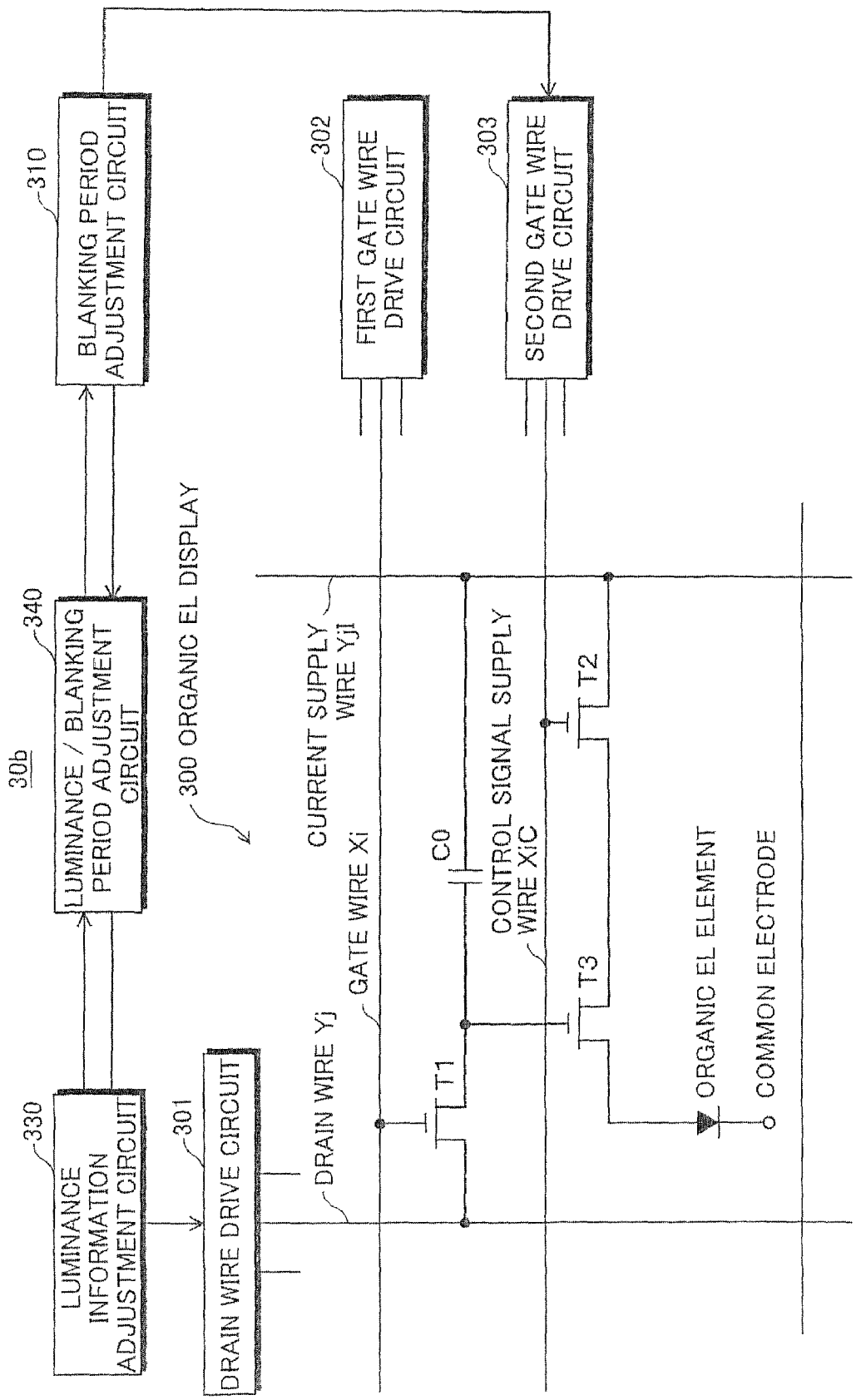
FIG. 8 shows a configuration example of a display unit used in the fourth embodiment of the present invention.

FIG. 8 shows a configuration example of a display unit used in the fourth embodiment of the present invention. In a display unit 30b, a luminance information adjustment circuit 330 and a luminance/blanking period adjustment circuit 340 are added to the display unit 30 according to the first embodiment as shown in FIG. 1. The rest of the configuration is the same as that of the first embodiment.

The luminance information adjustment circuit 330 adjusts luminance of the image signals generated by the B-mode image signal generating unit 25 (FIG. 1), and supplies the image signals having adjusted luminance to the drain wire drive circuit 301. The luminance/blanking period adjustment circuit 340 controls the luminance information adjustment circuit 330 and the blanking period adjustment circuit 310 to optimize the luminance and the ratio of the blanking period in the image signals.

For example, the luminance/blanking period adjustment circuit 340 controls the luminance information adjustment circuit 330 to change the levels of the image signals supplied to the drain wires Yj according to the ratio of the blanking period to the image display period adjusted by the blanking period adjustment circuit 310. Specifically, the luminance/blanking period adjustment circuit 340 controls the luminance information adjustment circuit 330 to increase the luminance of the image signals when the ratio of the blanking period is increased by the blanking period adjustment circuit 310. Thereby, even when the blanking period changes, the change of the brightness of the display image can be suppressed.

Next, the fifth embodiment of the present invention will be explained.

Figure 9:
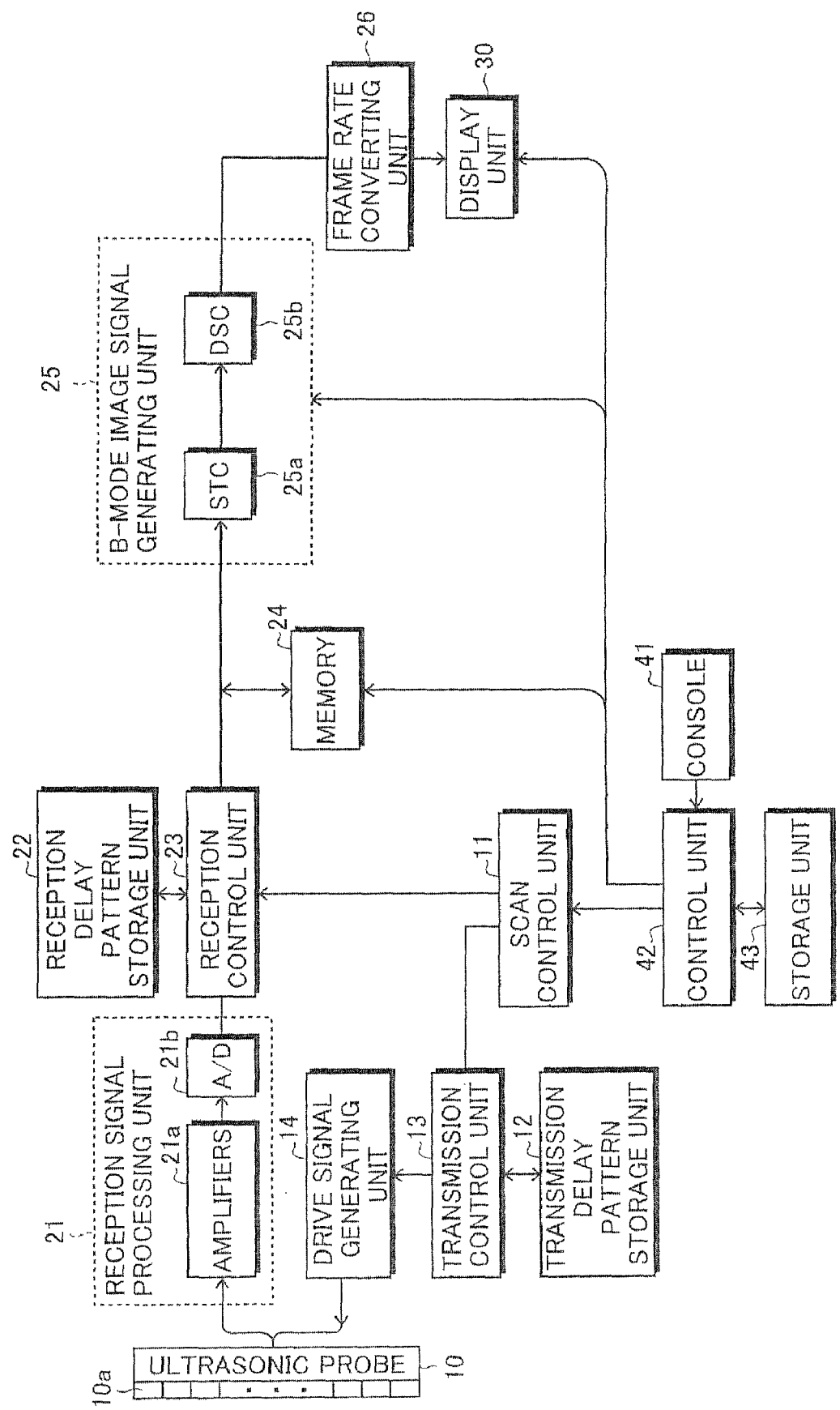
FIG. 9 is a block diagram showing a configuration of an ultrasonic diagnostic apparatus according to the fifth embodiment of the present invention.

FIG. 9 is a block diagram showing a configuration of an ultrasonic diagnostic apparatus according to the fifth embodiment of the present invention. In the fifth embodiment, a frame rate converting unit 26 is added to the ultrasonic diagnostic apparatus according to the first embodiment as shown in FIG. 1. The rest of the configuration is the same as that of the first embodiment.

Figure 10:
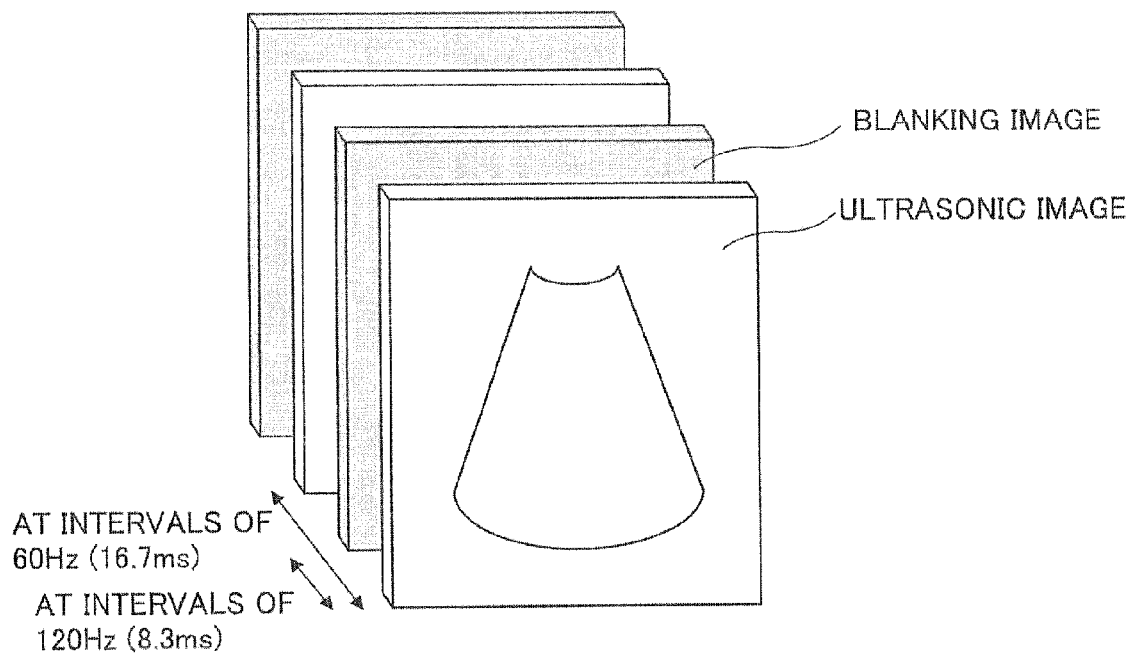
FIG. 10 is a diagram for explanation of an operation of the ultrasonic diagnostic apparatus according to the fifth embodiment of the present invention.

The frame rate converting unit 26 inserts image signals representing blanking images (preferably, having the black level) into the image signals representing the ultrasonic images, and thereby, generates image signals having a higher frame rate than that of the image signals generated by the B-mode image signal generating unit 25. For example, as shown in FIG. 10, the frame rate converting unit 26 inserts frames of blanking images between frames of ultrasonic images having a frame rate of 60 Hz, and thereby, generates moving images having a frame rate of 120 Hz to allow the display unit 30 to display the moving images. In this case, in the case where the rate of the image display period in the image signal generated by the B-mode image signal generating unit 25 is 100%, the rate of the image display period in the image signal generated by the frame rate converting unit 26 becomes 50%.

The invention claimed is:

1. An ultrasonic diagnostic apparatus comprising:
   an ultrasonic probe including plural ultrasonic transducers for transmitting ultrasonic waves toward an object to be inspected according to drive signals and receiving ultrasonic echoes propagating from the object to output reception signals;
   an image generating unit for supplying the drive signals to said ultrasonic probe and processing the reception signals outputted from said ultrasonic probe to generate image signals representing ultrasonic images;
   a display unit including a display of an impulse drive type, in which a blanking period within one field period is variable, for displaying the ultrasonic images based on the image signals generated by said image generating unit, and an adjustment circuit for adjusting a ratio of the blanking period to an image display period within one field period in said display; and
   a control unit for controlling said adjustment circuit to adjust the ratio of the blanking period to the image display period within one field period in said display according to at least one of a selected part to be examined and a frame rate of the image signals generated by said image generating unit.

2. The ultrasonic diagnostic apparatus according to claim 1, wherein said control unit further controls said adjustment circuit to adjust the ratio of the blanking period to the image display period within one field period in said display according to whether an ultrasonic image to be displayed in said display is a moving image or a still image.

3. The ultrasonic diagnostic apparatus according to claim 1, wherein said display unit includes an organic EL (electro luminescence) display.

4. The ultrasonic diagnostic apparatus according to claim 3, wherein:
   said display includes an image display period control circuit for generating a control signal to be activated in an image display period of each line, and an organic EL element, first to third thin-film transistors, and a holding capacity provided in each pixel;
   said first thin-film transistor allows said holding capacity to hold an image signal supplied via a drain wire according to a gate voltage supplied via a gate wire;
   said second thin-film transistor electrically connects a drain of said third thin-film transistor to a current supply wire according to the control signal generated by said image display period control circuit; and
   said third thin-film transistor supplies a current from a source to said organic EL element according to the image signal held in said holding capacity when the drain is electrically connected to said current supply wire.

5. The ultrasonic diagnostic apparatus according to claim 4, wherein said display unit further includes a second adjustment circuit for changing a level of an image signal supplied to the drain wire according to the ratio of the blanking period to the image display period adjusted by said adjustment circuit.

6. The ultrasonic diagnostic apparatus according to claim 1, further comprising:
   a frame rate converting unit for generating image signals having a higher frame rate than that of the image signals generated by said image generating unit by inserting image signals representing blanking images into the image signals representing the ultrasonic images.

7. The ultrasonic diagnostic apparatus according to claim 1, wherein said control unit controls said adjustment circuit to adjust the ratio of the blanking period to the image display period within one field period in said display according to a selected part to be examined.

8. The ultrasonic diagnostic apparatus according to claim 1, wherein said control unit controls said adjustment circuit to adjust the ratio of the blanking period to the image display period within one field period in said display according to a frame rate of the image signals generated by said image generating unit.

9. The ultrasonic diagnostic apparatus according to claim 1, wherein said control unit determines whether or not said ultrasonic diagnostic apparatus has been set into an energy saving mode, and controlling said adjustment circuit to adjust the ratio of the blanking period to the image display period within one field period in said display according to a determination result.

10. The ultrasonic diagnostic apparatus according to claim 1, further comprising:
a power supply voltage measurement circuit for measuring a power supply voltage at an external power supply input terminal;
wherein said control unit determines whether said ultrasonic diagnostic apparatus is battery driven or external power supply driven based on the power supply voltage measured by said power supply voltage measurement circuit, and controls said adjustment circuit to adjust the ratio of the blanking period to the image display period within one field period in said display according to a determination result.

11. The ultrasonic diagnostic apparatus according to claim 1, wherein:
said display unit further includes a brightness sensor for sensing brightness around said display; and
said adjustment circuit automatically adjusts the ratio of the blanking period to the image display period within one field period in the display according to a sensing result of said brightness sensor.

* * * * *